United States Patent [19]

Croce

[11] Patent Number: 5,198,338
[45] Date of Patent: Mar. 30, 1993

[54] MOLECULAR PROBING FOR HUMAN T-CELL LEUKEMIA AND LYMPHOMA

[75] Inventor: Carlo M. Croce, Philadelphia, Pa.

[73] Assignee: Temple University, Philadelphia, Pa.

[21] Appl. No.: 358,808

[22] Filed: May 31, 1989

[51] Int. Cl.⁵ .............................................. C12Q 1/68
[52] U.S. Cl. ......................................... 435/6; 435/91; 435/172.3; 436/501; 436/63; 436/64; 436/178; 436/813; 514/44; 536/24.31; 536/24.33; 935/10; 935/19; 935/27; 935/78; 935/88
[58] Field of Search .......................... 435/6, 91, 172.3; 436/501, 63, 64, 178, 813; 536/27; 935/10, 19, 27, 78, 88; 514/44

[56] References Cited

PUBLICATIONS

Science, vol. 237, Jul. 10, 1987, M.-S. Lee et al.: "Detection of minimal residual cells carrying the t(14;18) by DNA sequence amplification", pp. 175-178.

P.N.A.S. USA, vol. 86, Jun. 1989, J. Kagan et al.: "Clustering of breakpoints on chromosome 10 in acute T-cell leukemias with the t(10;14) chromosome translocation", pp. 4161-4165.

Croce, et al., "Gene a alpha-chain of Human T-Cell Receptor: Location on Chromosome 14 Region Involved in T-Cell Neoplasms," Science, (1985), 227:1044-1047.

Isobe, et al., "Cloning of the Gene Encoding the beta subunit of the Human T-Cell Receptor Reveals its Physical Organization Within the alpha-Subunit Locus and its Involvement in Chromosome Translocations in T-Cell Malignancy, " Proc. Natl. Acad. Sci. USA (1988), 85:3933-3937.

Zech, et al., "Inversion of Chromosome 14 Marks Human T-Cell Chronic Lymphocytic Leukaemia, " Nature, (1984), 308:858-860.

Erikson, et al., "Locus of the alpha-Chain of the T-Cell Receptor is Split by Chromosome Translocation in T-Cell Leukemias, " Science, (1985), 229:784-786.

Chien, et al., "A new T-Cell Receptor Gene Located Within the Alpha Locus and Expressed Early in T-Cell Differentiation, " Nature, (1987), 327:677-682.

Hata, et al., "Identification of Putative Human T-Cell Receptor beta Complementary DNA Clones, " Science, (1987), 238:678-682.

Boehm, et al., "The Mechanism or Chromosomal Translocation t(11;14) Involving the T-Cell Receptor C beta Locus on Human Chromosome 14q11 and a Transcribed Region of Chromosome 11p15, " EMBO J., (1988), 7:385-394.

Boehm, et al., "A Cluster of Chromosome 11p13 Translocations Found Via Distinct D-D and D-D-J Rearrangements of the Human T Cell Receptor beta Chain Gene, " EMBO J., (1988), 7:2011-2017.

Hecht, et al., "Common Region on Chromosome 14 in T-Cell Leukemia and Lymphoma, " Science, (1984), 226:1445-1446.

Dube, et al., "A New Translocation, t(10;14)(q24;q11), in T Cell Neoplasia, " Blood, (1986), 67:1181-1184.

Kagan, et al., "alpha-Chain Locus of the T-Cell Antigen Receptor is Involved in the t(10;14) Chromosome Translocation of T-Cell Acute Lymphocytic Leukemia, " Proc. Natl. Acad. Sci. USA, (1987), 84:4543-4546.

Primary Examiner—Amelia Burgess Yarbrough
Assistant Examiner—Ardin H. Marschel
Attorney, Agent, or Firm—Banner, Birch, McKie & Beckett

[57] ABSTRACT

A very specific area of chromosome 10, band q11 is taught to be the site of chromosome breakpoints which occur in the course of translocations. The translocation brings sequences of the T-cell antigen receptor delta locus into adjacency with the specific area on chromosome 10. The area of chromosome 10 is presumed to carry an oncogene which is activated by the proximity to the delta locus. Methods and molecular probes and primers are taught for determining the presence of this particular translocation.

16 Claims, 8 Drawing Sheets

HindIII

BamHI

FIG. 5

```
                              CH. 14 GERMLINE    GAAGTTTTTGTAAAGC
                                                    ||||||||||||||
CH. 10Q⁺ JM/BP      5' TCTGTCTCGGCTTCTCTGGCCTTCCTCTCCCCCTCCCCCTCGCGCTGTCAT
                       ||||||||||||||||||||||||||||||||||||||||||||||||||
CH. 10 GERMLINE     5' TCTGTCTCGGCTTCTCTGGCCTTCCTCTCCCCCTCCCCCTCGCGCTGTCAT
                       ||||||||||||||||||||||||||||||||||||||||||||||||||
CH. 10Q⁺ DW B/P     5' TCTGTCTCGGCTTCTCTGGCCTTCCTCTCCCCCTCCCCCTCGCGCTGTCAT

CAATTGGGATAAAAGTTGACTCTGATAAACAAAAAGGTAGGAGGGAAAAGGAAG

GAGCTTGACAGTCTTAGTGGGCCATGTACAAGGAGTGGTGACTCTGCCAACCTTAAG
                                                 CH. 14 GERMLINE  GAAGTTTTTGTAAAGCTCTGTAG
                                                                    |||||||||||||||||||||
                           Dδ2
 TCTGTAGCCACTGTGACTGGGGATACGCACAGTGCTACAAAAACCTACAGAGAGACCTGTACAAAAACTGCA
                    |||||||||||||||||||||||||||||||||||||||||||||||||||||||
      AGCCACTGTGACTGGGGATACGCACAGTGCTACAAAAACCTACAGAGAGACCTGTACAAAAACTGCA
 TCACCCCGCTCCCCCCACAGGGATACGCACAGTGCTACAAAAACCTACAGAGAGACCCAGTGCGAAACCGCGAACGTCTCTT
                    |||||||||
 TCACCCCGCTCCTCTCCGCGCACAGCCAATGGAGAGACTCACAGAATCCAGCACCTCATTGAGGGTAAAAGTTGGGAGTATCC

TCACCCCGTAAGCTGACTGGTGCAGGGCTGTGACTGCGCAGGGGAAAGTCAGTTCAGTATATCCCTGGTGCTGGATTTTAATGAGAA
 AAATCCGTCAAGGAAGCGGGCTGTGACTGCGCAGGGGAAAGTCAGTTCAGTATATCCCTGGTGCTGGATTTTAATGAGAA

CTGGGCCAAAAGGGGATACGCACAGTGCTACAAAAACCTACAGAGAGACCTGTACAAAAACTGCA
           ||||||||||||||||||||||||||||||||||||||||||||||||||||||||
 CACTGTGACTGGGGATACGCACAGTGCTACAAAAACCTACAGAGAGACCTGTACAAAAACTGCA
    Dδ2
```

MOLECULAR PROBING FOR HUMAN T-CELL LEUKEMIA AND LYMPHOMA

The U.S. Government has a paid-up license in this invention and the right in limited circumstances to require the patent owner to license others on reasonable terms as provided for by the terms of grant No. CA 39860 from the National Cancer Institute.

TECHNICAL FIELD OF THE INVENTION

The invention relates to the area of cancer diagnosis and prognosis. More particularly, it relates to the field of T-cell malignancies which are caused by chromosome translocation t(10;14) (q24; q11).

BACKGROUND OF THE INVENTION

Chromosomal abnormalities, translocations, inversions and deletions are nonrandomly associated with certain types of human leukemias and lymphomas (Yunis, J., 1982, Science 221:227-236). In T-cell tumors, many such abnormalities involve the T-cell receptor alpha locus (TCR alpha) at chromosome band 14 q11 (Croce, C. M., et al., 1985, Science 227:1044-1047; Isobe, M., et al., 1988, Proc. Natl. Acad. Sci. USA 85:3933-3937; Zech, L., et al., 1984, Nature 308:858-860; Erickson, J., et al., 1985, Science 229:784-786). The TCR delta locus was identified between the 5' portion of the alpha chain J segments and the V alpha segments (Chien, Y., et al., 1987, Nature 327:667-682; Hata, S., et al., 1987, Science 238:678-681). By means of somatic cell hybrids and molecular cloning of the entire delta locus (Isobe, M., et al., 1988, Proc. Natl. Acad. Sci. USA 85:3933-3937; Boehm, T., et al., 1988, EMBO J. 7:385-394), the direct involvement of the J delta-D delta segments in t(11;14) and t(8;14) chromosome translocations in T-cell malignancies was demonstrated (Isobe, M., et al., 1988, Proc. Natl. Acad. Sci. USA 85:3933-3937; Boehm, T., et al., 1988, EMBO J. 7:385-394; Boehm, T., et al., 1988, EMBO J. 7:2011-2017).

The t(10;14) (q24; q11) chromosome translocation has been described in acute T-cell leukemias and high-grade T-cell lymphomas (Hecht, F., et al., 1984, Science 226:1445-1446; Dube, I. D., et al., 1986, Blood 67:1181-1184; Kagan, J., et al., 1987, Proc. Natl. Acad. Sci. USA 84:4543-4546). Cells derived from three different patients with acute T-cell leukemia were analyzed and the breakpoint in this translocation was found within the TCR alpha locus in the region between the C alpha and V alpha genes on chromosome 14 (Kagan, J., et al., 1987, Proc. Natl. Acad. Sci. USA 84:4543-4546). Isobe, et al., 1988, Proc. Natl. Acad. Sci. USA, pp. 3933-3937, reported that in one case of T-cell leukemia/lymphoma carrying the t(10;14) (q24; q11) translocation, the TCR delta locus was found to be rearranged.

The only diagnostic test for the t(10;14) translocation now available is cytogenetic analysis which is labor intensive, expensive, and often unsuccessful. Thus, there is a need in the art for further definition of the chromosome translocation breakpoint sites involved in T-cell malignancies so that simpler and more rapid tests can be devised for diagnosis of these diseases.

SUMMARY OF THE INVENTION

It is an object of the invention to provide a method for diagnosing and prognosing a T-cell malignancy.

It is another object of the invention to provide nucleic acid probes which hybridize to regions of chromosome 10 adjacent to the chromosome translocation breakpoint associated with acute T-cell lymphoblastic leukemia and high grade T-cell lymphoma.

It is still another object of the invention to provide single-stranded nucleic acid primers for amplification of a region of DNA containing a translocation chromosome junction associated with acute T-cell lymphoblastic leukemia and high grade T-cell lymphoma.

These and other objects of the invention are provided by one or more embodiments of the invention described below. In one embodiment a method is provided for diagnosing and prognosing a T-cell malignancy in a human comprising: isolating DNA from the T-cells of the human; determining whether sequences of said DNA isolated from said T-cells at the region of chromosome 10 containing a chromosome breakpoint cluster diverges from germline sequences, divergence of said sequences indicating a T-cell malignancy.

In another embodiment a nucleic acid probe is provided which hybridizes to a region of chromosome 10 between a chromosome translocation breakpoint cluster associated with acute T-cell lymphoblastic leukemia and high grade T-cell lymphoma and a cleavage site for a restriction enzyme, wherein there are no other cleavage sites for said restriction enzyme between the breakpoint cluster and the site for the restriction enzyme.

In still another embodiment of the invention a pair of single-stranded nucleic acid primers are provided for amplification of a region of DNA containing a translocation chromosome junction associated with acute T-cell leukemia and high grade T-cell lymphoma, one of said primers derived from chromosome 10 and one of said primers derived from chromosome 14, both of said primers hybridizing to sequences retained on a 10q+ chromosome resulting from a t(10:14) (q24;q11) translocation.

The present invention provides the art with a simple, inexpensive, and reproducible means of diagnosing and prognosing T-cell malignancies associated with translocations of chromosomes 10 and 14. In addition, it provides the art with a means of monitoring the response of the malignant T-cells to therapy.

BRIEF DESCRIPTION OF THE DRAWINGS

FIG. 5 reveals the nucleotide sequence of the joining site between chromosomes 10 and 14 in JM and DW leukemic T-cells and the corresponding chromosome 10 germline region. Vertical lines indicate identical nucleotides in the D-delta-2-diversity segment of the TCR delta as well as identical nucleotides in the chromosome 10 region adjacent to the translocation breakpoint cluster. The bracketed regions are conserved heptamer-nonamer signal sequences.

DETAILED DESCRIPTION

Figure 1A:
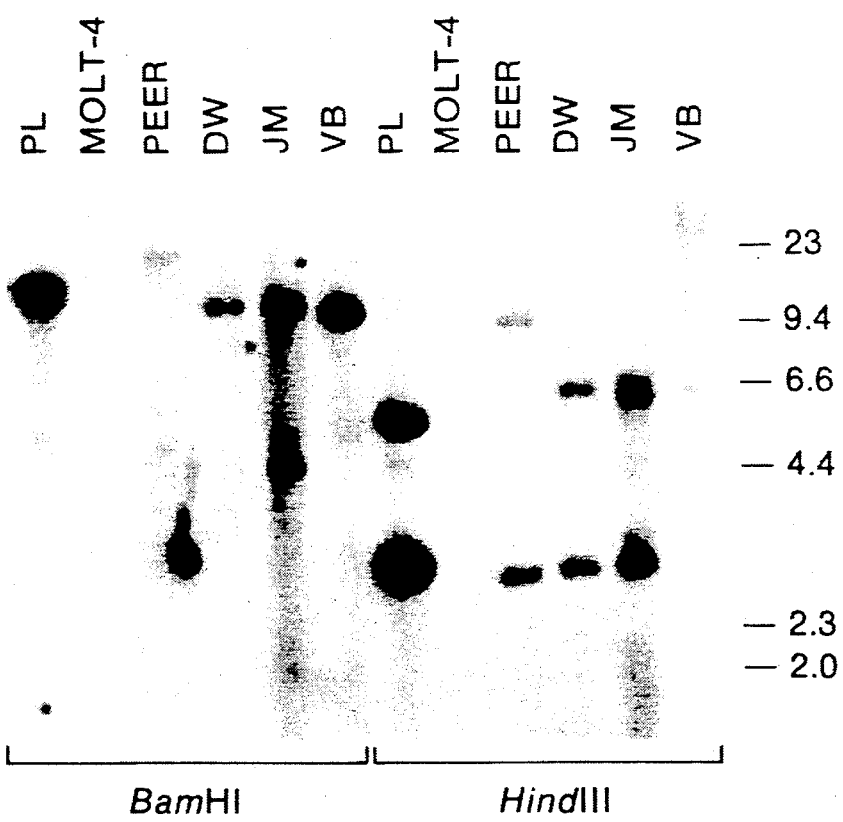
FIG. 1(A) shows rearrangements of the human TCR J delta locus in DNA from patients DW, JM and VB carrying the t(10;14) (q24;q11) chromosome translocation and in T-cell lines PEER and Molt-4. PL, placental DNA. The Southern blot was probed with pjk3.0 SacI. Molecular weight is given in kb. (B) shows a restriction enzyme map of the TCR delta locus and probes utilized in the present study. E, EcoRI; H, HindIII; B, BamHI; S, SacI.

It is a finding of the present invention that translocations between chromosomes 10q24 and 14q11 which are associated with malignancies of the T-cell lineage, such as acute T-cell leukemia and high grade T-cell lymphoma, have breakpoints clustered to two well-defined loci. On chromosome 14, the translocation breakpoints are all in the D-delta-2 region of the T-cell antigen receptor. On chromosome 10, the translocation breakpoints are clustered to a region of about 263 bp. This finding allows nucleic acid probes and primers to be designed and made for detecting translocations among the DNA of lymphocytes. Such probes and primers can be used without recourse to cytogenetic examination.

A chromosome breakpoint cluster, according to the present invention is a region of the chromosome which is consistently involved in translocations associated with T-cell malignancies, such as acute T-cell leukemia and high grade T-cell lymphoma. It is the region of the chromosome which is joined directly to sequences of another chromosome to form a translocation chromosome junction. Two translocation breakpoints on each of chromosomes 10 and 14 are depicted in FIG. 5 which define the clusters. The breakpoints on chromosome 10 are those sequences immediately 5' to the D-delta-2 segment (see, Boehm et al., The EMBO Jour., vol. 7, pp. 2011-2017, 1988,) on the 10q+ chromosomes of DW and JM. On chromosome 14, the breakpoints of DW and JM are at the D-delta-2 sequences in essentially the same place. Thus probes can be derived from sequences on either side of the breakpoint clusters on either chromosome 10 or chromosome 14 for use in detecting translocations. Primers should generally be derived from either side of a translocation chromosome junction. The breakpoint cluster on chromosome 14 is located on a 16.5 kb BamHI fragment which hybridizes to the probes pjk delta1 0.65S, p101-delta-1 5.0E, p101.j-delta-1-e50, pjk3.0S, and pjk delta2 2.4 E/B. Probe p101.j-delta-1-e50 is on deposit at the ATCC as deposit no. 67996. The breakpoint cluster on chromosome 10 is located on a 5.7 kb BamHI fragment which hybridizes to pjk 1.7 E/B (NRRLB-18501).

DNA is isolated from the T-lymphocytes (T-cells) of the humans to be tested, according to the present invention. T-lymphocytes generally do not need to be purified from other blood cells because of their preponderance in the case of T-cell malignancies. However, T-cells can be isolated to increase sensitivity of the method. Means of obtaining T-lymphocytes are also well known in the art. Generally, they are isolated from the peripheral blood of a patient and separated on the basis of size or density. Any DNA isolation method known in the art may be used. Generally, the cells are lysed and DNA is extracted from other cellular components, such as proteins. Solvent extractants can be used or physical means such as density gradient centrifugation may be used to isolate DNA from other cellular components. Choice of methods for isolating DNA is within the skill of the art.

In order to determine the presence of chromosomes carrying the t(10;14) (q24;q11) translocation, a comparison can be made control DNA containing germline sequences. This can be done using DNA isolated from placental tissue or from non-T-cell tissue of the human to be tested, or from another healthy human. Divergence between the T-cell sequences and the control DNA containing the germline sequences at the region of chromosome 10 containing the chromosome breakpoint cluster being diagnostic for T-cell malignancy.

The divergence from germline chromosome 10 sequences in the T-cell DNA can be confirmed by screening the same T-cell DNA to determine whether the sequences which diverge are derived from chromosome 14. The breakpoint cluster on chromosome 14 is in the D-delta-2 segment of the T-cell antigen receptor (TCR) delta locus.

Methods for determining sequence divergence between the DNA isolated from the human T-cell and germline sequences can be according to any means known in the art. These include Southern hybridization, polymerase chain reaction, and molecular cloning and sequencing. Each of these techniques are well known, and choice of technique is within the skill of the practitioner. Sequence divergence for the purposes of the present invention is a gross genetic change, such as is due to translocation, deletion, insertion, or inversion. Simple point mutations do not cause sequence divergence as used herein.

In the case of Southern hybridization, DNA isolated from T-cells, as described above, is cleaved with a restriction enzyme to form DNA fragments having discrete endpoints. The DNA fragments are separated electrophoretically and hybridized to a nucleic acid probe. The nucleic acid probe may be an RNA or a DNA probe and may be labeled according to any means known in the art. Typically the probe will be radioactivately labeled, although other labels such as fluorescent labels are also suitable. The nucleic acid probe can be derived from sequences adjacent to either of the translocation breakpoint clusters, on chromosome 10 or on chromosome 14. The adjacent sequences are any of a suitable hybridizable length (generally longer than 15 nucleotides) which lie between the chromosome breakpoint cluster or translocation chromosome junction and a site for a restriction enzyme. There should be no other sites for the restriction enzyme between the breakpoint cluster or junction and the probe. Thus, the adjacent sequences from which the probe is derived must lie on a restriction enzyme fragment which contains at least part of the translocation breakpoint cluster.

A particularly preferred nucleic acid probe is plasmid pjk1.7E/B, or a fragment thereof, which hybridizes to chromosome 10. Plasmid pjk1.7E/B is deposited at the Agricultural Research Culture Collection (NRRL), Peoria, Ill., and has been assigned accession no. B-18501. The restriction enzyme BamHI can be used to isolate a fragment containing both pjk1.7E/B hybridizing sequences and the translocation breakpoint cluster. Preferred probes from chromosome 14 are derived from the TCR locus J-delta-1 segment. One such probe, p101.j-delta-1-e50 is on deposit at the American Type Culture Collection (ATCC), Rockville, Md., and has been assigned accession no. 67996. BamHI can be used to isolate J-delta-1 sequences on a single restriction fragment with the translocation breakpoint cluster, as it does not cleave chromosome 14 in or between the D-delta-2 and J-delta-1 segments. Other restriction enzymes with similar properties with respect to cleavage of chromosome 14 can be used.

The size of the T-cell DNA fragments which hybridize to the probe is determined, and compared to the size obtained when a control DNA is used. The control DNA may be any which contains the germline sequences. This can be from non-lymphocytes of the human patient, from placental tissue, or from any tissue of a human who is healthy (carries no t(10;14) translocation). If the size of the hybridizing fragments from the patient T-cell DNA is different from the control fragments, the DNA sequences of the T-cells and the germline must diverge, to account for the changed fragment size. Divergence of the sequences is an indication of T-cell malignancy. Divergence may also be due to deletions which could be associated with oncogenesis.

In another method for determining divergence between T-cell and germline sequences at a chromosome 10 breakpoint cluster associated with T-cell leukemia and high grade T-cell lymphoma, the polymerase chain reaction is used to amplify DNA isolated from T-cells of a human patient. This reaction is well known in the art. See, e.g., Saiki, et al., Science, vol. 239, p. 487, 1988, U.S. Pat. No. 4,683,203, and U.S. Pat. No. 4,683,195. It is desirable that a discrete region of DNA which spans the translocation chromosome junction between chromosomes 10 and 14 associated with acute T-cell leukemia and high grade T-cell lymphoma be amplified. The translocation junction is shown in FIG. 5 in detail. In order to amplify, two single-stranded primers are used. In a preferred embodiment one primer hybridizes with chromosome 10 sequences and the other with chromosome 14 sequences; both primers hybridize to a 10q+ chromosome resulting from a t(10;14) (q24;q11) translocation. Using such a set of primers, an amplified band will only be detected when a translocation has occurred. The amplified band is evidence that a translocation has occurred between chromosome 10 and 14.

Preferred primers in the practice of the present invention are derived from plasmid pjk1.7E/B sequences. If a primer from each of chromosomes 10 and 14 are used as a pair using DNA carrying a translocation as a template, an amplified band would be expected; however, no amplified band would be expected in the control or germline sequences. If a primer pair from either side of the chromosome 10 breakpoint cluster were used, it would be possible to detect deletions which may occur in this region and which may be associated with T-cell malignancies.

After amplification of sequences, the size of amplified DNA can be determined by electrophoresis, e.g., on agarose gels. The amplified band can be visualized directly by ethidium bromide/ultaviolet light or can be detected by hybridization to a probe, e.g., a radiolabeled DNA probe. Such techniques are well known in the art.

Also contemplated by the present invention are the nucleic acid probes and primers for use in the methods of diagnosis and prognosis of T-cell malignancy. The probes can be double or single-stranded, deoxy- or ribonucleic acids. They may be isolated from biological sources by any means known in the art. They may be synthesized chemically. The probes may be radiolabeled or fluorescent labeled. All such techniques and choices are well within the skill of the art. Primers are generally synthesized chemically, although they can also be isolated and prepared from biological sources.

Probes are derived from DNA located between the chromosome breakpoint cluster region associated with acute T-cell leukemia and high-grade T-cell lymphoma (shown in FIG. 5) on either chromosome 10 or 14, and the first cleavage site for a particular restriction enzyme proximal to the breakpoint cluster. Thus when normal human DNA is cleaved with the particular restriction enzyme, the breakpoint cluster and the sequences hybridizing to the probe are located on a single fragment. Plasmid pjk1.7E/B is such a probe, useful in conjunction with enzyme BamHI. Probes derived from J-delta-1 of the TCR locus on chromosome 14, are also useful in conjunction with the enzyme BamHI.

Primers for amplification are generally single-stranded nucleic acids. Primers are derived from either side of a chromosome breakpoint cluster associated with acute T-cell leukemia and high-grade T-cell lymphoma. A pair of primers may both be derived from a germline chromosome 10, or may be derived from a 10q+ chromosome resulting from an acute T-cell leukemia-associated translocation. In the latter case, one primer would hybridize to germline chromosome 10, and one to germline chromosome 14.

The methods and nucleic acids of the present invention can be used to provide a diagnosis (e.g., acute T-cell leukemia) and a prognosis, (i.e., expected response to therapies, likelihood of remission, expected duration of disease.) There are indications that T-cell malignancies having t(10;14) translocations respond well to antineoplastic therapy. In addition, the methods and nucleic acids can be used to monitor the course of chemotherapy. If during or after chemotherapy some sequences remain detectable in the T-cell DNA population which diverge from germline sequences at the chromosome translocation breakpoint cluster, then chemotherapy should be continued or resumed, until no such divergent sequences are detected. Further, quantitation of the divergent sequences among a population of T-cells can be used to provide information as to the appropriateness and efficacy of particular doses and regimens of chemotherapy.

The following examples are provided for exemplification purposes only and do not limit the scope of the invention described above and in the claims which follow.

EXAMPLE 1

This example demonstrates that rearrangements are found in the TCR delta locus of chromosome 14 in T-cell lines and in patients with T-cell malignancies.

Neoplastic cells were obtained from three patients: DW, a patient with T-cell lymphoblastic leukemia/lymphoma with a karyotype 46, X, Y, t(10;14) (q24;q11); JM, a patient with acute T-cell leukemia with a karyotype of 47, X, Y, 12p−, +12p−, t(10;14) (q24;q11); and VB, a patient with T-cell non Hodgkin's lymphoma with a karyotype of 46, X, Y, −9, +der(9), t(9;16), t(10;14), −18, −19, −20, +der(20), +mar, +mar.

High molecular weight DNA was prepared and digested with restriction endonucleases for 5 hours, and 10–20 ug samples were fractionated on a 0.8% agarose gel (Sigma Chemical Co., St. Louis, Mo.). Transfer of DNA from gel to nitrocellulose sheet (Millipore) was performed essentially as described by Southern (Southern, E.M., 1975, J. Mol. Biol. 98:503–517). Hybridization probes were prepared by nick translation to specific activities (greater than $5 \times 10^8$ cpm/ug).

DNA on nitrocellulose sheets was hybridized to $^{32}$P-labelled probe DNAs in 0.6M NaCl, 60 mM sodium citrate (pH 7.0), 50% formamide at 37° C. for 18 hours. Final washes with 15M NaCl, 1.5 mM sodium citrate were followed by air drying and exposure to XAR-5 film (Kodak) for varying periods.

Figure 1B:
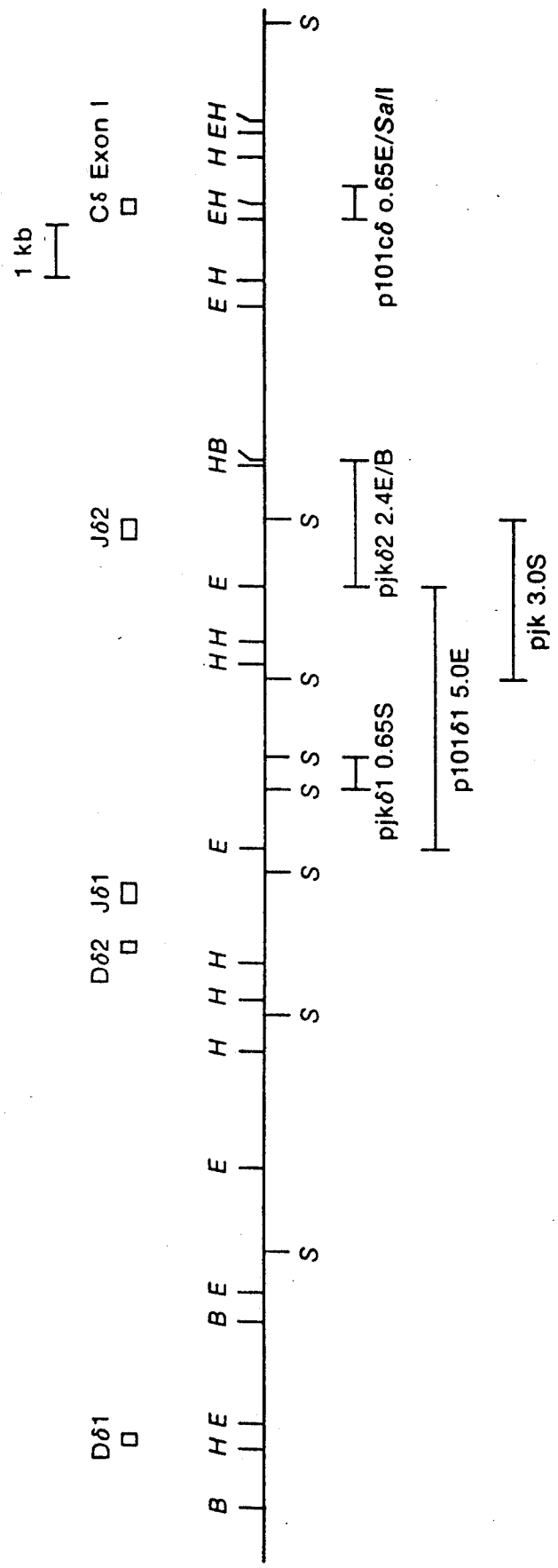

Using probe pjk3.0S (see FIG. 1B) for the TCR delta locus, we have detected genomic rearrangements in J delta on Southern blots of T-cell leukemias and lymphomas (FIG. 1A). The first type of rearranged fragments were detected in a control T-cell line, PEER, (Hata, et al., Science, 238:678–681, 1987) which expresses the gamma/delta TCR but does not have the t(10;14) (q24;q11) chromosomal translocation (Tsujimoto, Y., et al., 1985, Nature 315:340–343). These fragments corresponded to 20 kb BamHI and 12 kb HindIII, as compared to 16.5 kb BamHI and 5.8 kb HindIII and 3.2 kb HindIII germline fragments. Another control T-cell line, Molt-4, (available from the ATCC, Rockville, Md. as CRL 1582,) showed no hybridization with this probe and was deleted in the J delta region (two rearrangements were found in the J alpha region).

A 4.7 kb BamHI rearranged fragment which was detected in the DNA of one patient (JM) corresponds to physiological rearrangement at the J-delta-2 segment of TCR delta. A third type of rearrangement was detected in DNA samples derived from all three patients with the t(10;14) (q24;q11) chromosome translocation in their leukemic cells: identical rearranged 13.9 kb BamHI and 6.8 kb HindIII fragments (FIG. 1A). These latter results strongly suggest that if the rearranged fragments are due to the chromosome translocation, then all translocation breakpoints are clustered in a very narrow region.

EXAMPLE 2

This example demonstrates that the TCR delta locus is directly involved in t(10;14) (q24;q11) chromosome translocations.

Leukemic T-cells from two patients (DW and JM) carrying the t(10;14) (q24;q11) chromosome translocation were fused with mouse leukemic BW5147 T-cells deficient in hypoxanthine phosphoribosyl transferase using polyethylene glycol. Hybrids were selected in hypoxanthine/aminopterin/thymidine (HAT) medium according to standard procedures (Erikson, J., et al., 1985, Science 229:784–786; Erikson, J. et al., 1986, Science 232:982–985).

Hybrids thus obtained were examined for genetic markers of human chromosome 10 and 14. Hybrid 648 was derived from JM leukemic T-cells, while hybrid 639 was derived from DW leukemic T-cells as described previously (Kagan, J., et al., 1987, Proc. Natl. Acad. Sci., USA 84:4543–4546). Results of cytogenetic and Southern blot analyses of hybrids employed in the present study are summarized in Table I.

Chromosome preparations were made as previously described (Kagan, J., et al., 1987, Proc. Natl. Acad. Sci. USA 84:4543–4546); at least 25 metaphases were examined for each hybrid. Selected metaphases were studied by G11 banding technique (Erickson, et al., Proc. Natl. Acad. Sci. USA, 79:5611–5615, 1982) to confirm the human origin of the relevant chromosomes.

The expression of nucleotide phosphorylase (NP), the gene which is proximal to TCR alpha on chromosome 14, was studied by starch gel electrophoresis (Erikson, J., et al., 1985, Science 229:784–786; Erikson, J., et al., 1986, Science 232:982–985).

DNA probes used included: 1) for variable region of TCR alpha (V alpha), an AvaI-PstI fragment isolated from pHaT3 cDNA clone (Kagan, J., et al., 1987, Proc. Natl. Acad. Sci. USA 84:4543–4546); 2) for the immunoglobulin heavy chain joining region, pHj was used (Kagan, J., et al., 1987, Proc. Natl. Acad. Sci. USA 84:4543–4546); 3) and for the enzyme terminal deoxynucleotidyltransferase (TdT), pt106 was used (Isobe, M., et al., 1985, Science 227:5836–5840); 4) for the TCR delta joining region 1, p101 delta 5.0E shown in FIG. 1b was used.

TABLE I

| SEGREGATION OF HUMAN GENES IN JM-BW5147 HYBRIDS* | | | | | | | | | |
|---|---|---|---|---|---|---|---|---|---|
| | Human Genes | | | | | | Human Chromosomes | | |
| Cell Line | V alpha | J-delta-1 | NP | JH | TdT | 10 | 10q+ | 14 | 14q− |
| 639-AD4 | − | R | − | + | + | − | ++ | − | − |
| 648-8E10 | − | R | − | + | + | − | ++ | − | − |
| 648-BD4 | + | R | + | + | + | ± | ++ | + | + |
| 648-CC6 | + | D | + | + | + | ++ | − | ++ | − |
| 648-AC4 | + | + | + | + | − | − | − | ++ | − |
| 648-28F4 | + | D | + | + | − | − | ± | + | ++ |
| 648-AA3 | + | D | + | + | − | ± | ± | + | ± |

NP = nucleotide phosphoribase; V alpha = variable region of TCR alpha; JH = immunoglobulin heavy chain joining region; TdT = terminal deoxynucleotidyltransferase; J-delta-1 = TCR alpha joining region 1 (p101 dleta 5.0E in FIG. 1); R = rearranged; D = deleted.
Frequency of metaphases with relevant human chromosome: − = none; ± = less than 10%; + = 10-30%; ++ = greater than 30%.

Hybrids 648-8E10 and 639-AD4 contained only the 10q+ chromosome, having lost the other three relevant human chromosomes (10, 14 and 14q−). Hybrid 648BD4 retained all the relevant chromosomes, while hybrid 648CC6 retained chromosomes 10 and 14. Hybrid 648AA3 retained chromosome 14 and a low frequency of 10, 10q+ and 14q−. Hybrid 648AC4 contained chromosome 14 only. Hybrid 648-28F4 retained chromosomes 14 and 14q− and a low frequency of 10q+, which was not detected on Southern blot by the relevant genetic marker [terminal deoxynucleotidyl transferase (TdT) gene].

Figure 2:
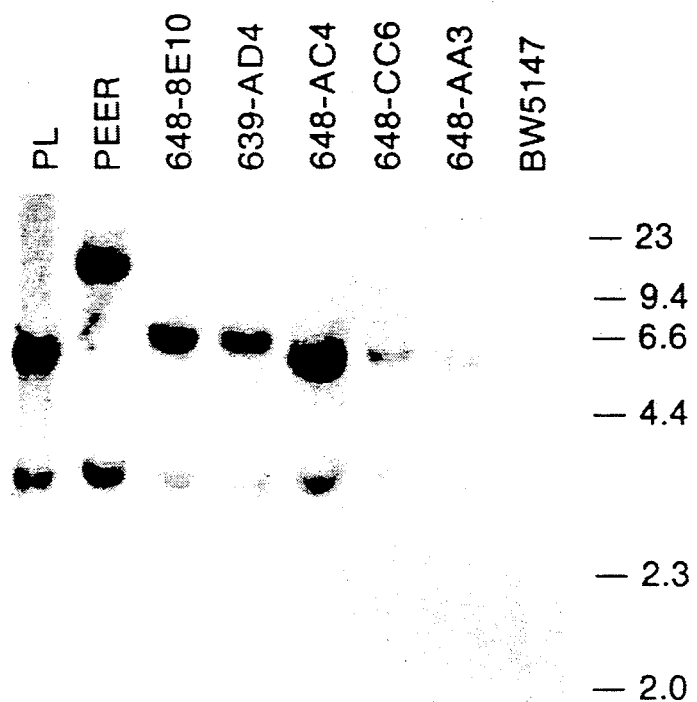
FIG. 2 depicts a Southern blot hybridization of HindIII-digested hybrid clone DNAs with J-delta-1 probe p101 delta 5.0E. PL is placental DNA. Molecular weight is given in kb.
Figure 3A:
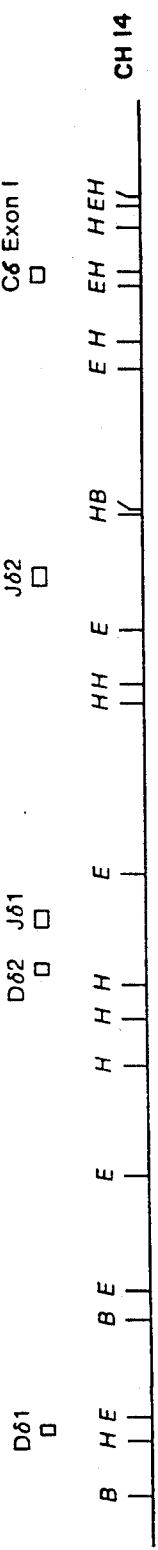
FIG. 3 shows restriction maps of the regions surrounding the breakpoint in two different t(10;14) q24;q11) chromosome translocations. (A) The germline TCR delta locus on chromosome 14. (B) Restriction map of lambda W-2, a rearranged phage clone covering the translocation point isolated from DW's genome library. (C) Restriction map of lambda BD4-14, a rearranged lambda phage clone covering the translocation breakpoint, isolated from JM's hybrid 648-BD4 genomic library. (D) The germline chromosome 10 restriction map around the translocation point. Restriction maps of the germline chromosomes 10 and 14 were deduced from overlapping lambda phage clones isolated from placental DNA genomic library.
Figure 3B:
Figure 3C:
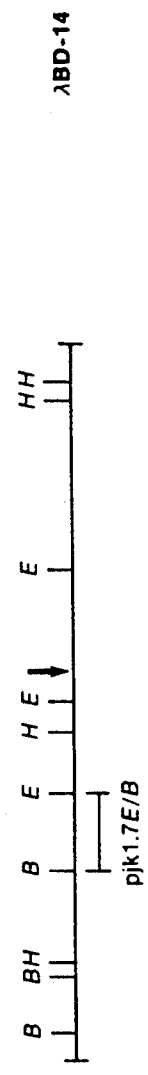
Figure 3D:

The breakpoint on chromosome 10 is distal to the TdT gene since hybrids 648-8E10 and 639AD4, which contained only the human 10q+ chromosome in the absence of other relevant human chromosomes, were positive for TdT. The human immunoglobulin heavy chain joining ($J_H$) region located at band 14q32 was detected in all hybrids containing the normal human chromosome 14 or the 10q+ (Table I). On chromosome 14, the translocation splits the TCR J delta locus between J-delta-1 and V alpha, since Southern blot analysis using probe p101J-delta-15.OE on hybrid 648-8E10 and 639AD4 DNA detected a rearranged 6.8 kb HindIII fragment and 3.2 kb HindIII germline fragment, while hybrids 648-AC4, 648CC6 and 648AA3 contained only the 5.8 kb HindIII and 3.2 kb HindIII germline fragments (FIG. 2 and Table I). Rehybridization of the same blot with the TCR V alpha probe revealed that the V alpha region segment was deleted from hybrids 648-8E10 and 639-AD4 (Table I), providing further indication that the breakpoint splits the J delta locus between the J-delta-1 and V alpha segments.

EXAMPLE 3

This example demonstrates additional evidence that the TCR delta locus is directly involved in t(10;14) (q24;q11) chromosome translocations.

Complete genomic libraries were constructed in the phage vector, EMBL3 (Tsujimoto, Science, 224:1403-1406, 1984), from partially Sau3A-digested DW leukemic T-cell DNA, hybrid 648 BD4 (derived from a fusion of JM's leukemic T-cells with mouse BW5147 cell line), and human placenta DNA. Restriction maps were prepared by single and double digestions of DNA and subclones prepared in pUC 19, PIBI25 and M13 vectors (available from BRL, Rockville, Md., and see Haluska, Nature 324:158-161, 1986).

Chromosome breakpoints were molecularly cloned from genomic libraries constructed from DW leukemic T-cells, JM hybrid 648-BD4 and human placental DNA. Using probes pjk3.0S and p101 delta 15.0E (see FIG. 1b) specific for the TCR J delta region, we were able to isolate eight overlapping phage clones which by restriction enzyme map analysis proved to have the rearranged fragments.

Restriction enzyme maps of lambda BD4-14 and lambda W-2, two representative clones derived from two of the three patients with a t(10;14) chromosome translocation in their leukemic cells, had identical rearranged fragments and matched the germline TCR J delta region at their 3' ends but diverged at their 5' ends (FIG. 3).

EXAMPLE 4

This example demonstrates that the origin of the DNA that differs from germline delta segment of TCR in lambda W-2 and lambda BD4-14, is from chromosome 10.

Figure 4A:
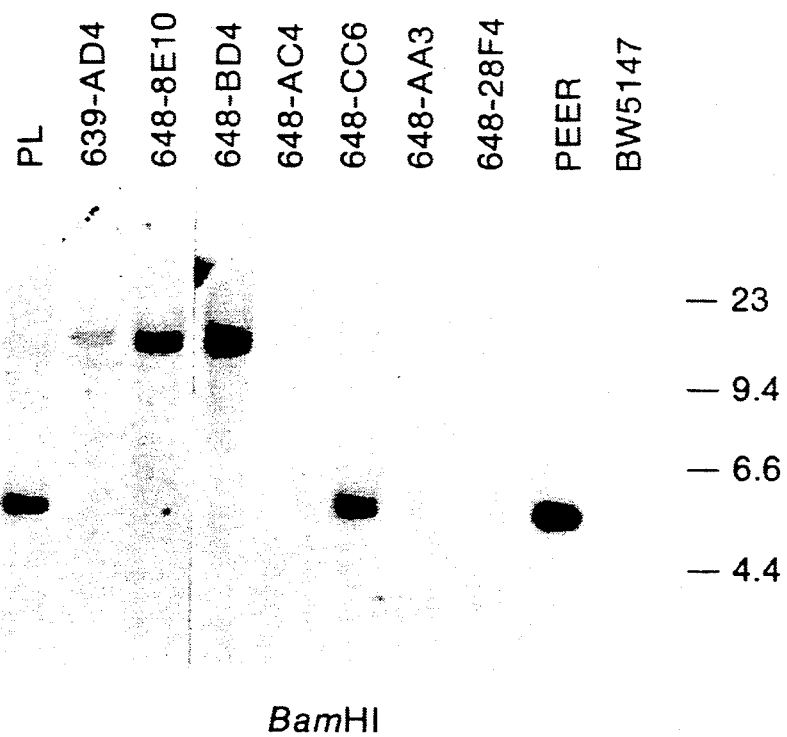
FIG. 4 demonstrates the detection of the rearranged fragment with a chromosome 10 probe. (A) Hybridization of HindIII-digested hybrid DNA panels with pjk1.7E/B. (B) Hybridization of HindIII-digested hybrid DNAs with TdT (pt106), a chromosome 10 probe. (C) Detection of the rearranged fragment in DNA from three different patients with t(10;14) (q24;q11) chromosome translocation with chromosome 10 probe. pjk1.7E/B, a chromosome 10 probe, was hybridized with the same Southern blot which was used previously to detect rearrangement in J delta region (FIG. 4A). PL is placental DNA. DW, JM, VB, are patients with the t(10;14) (q24;q11) chromosome translocation. Molecular weight is given in kb.

To determine the origin of the lambda W-2 and lambda BD4-14 DNA that differed from the J delta germline map, we subcloned a 1.7 kb EcoRI-BamHI fragment into plasmid vector pIBI25 and used it to probe a panel of BamHI-digested hybrids which were previously used to demonstrate the split in the TCR J delta locus; the results are presented in FIG. 4A.

Figure 4B:
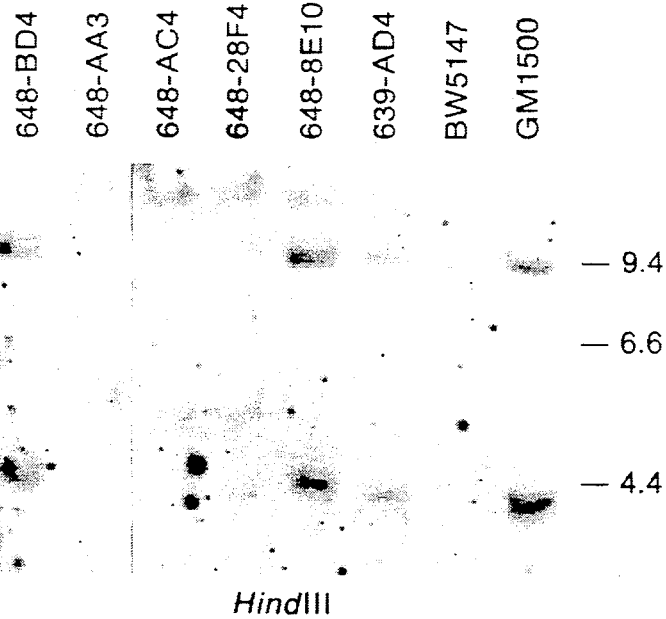
Figure 4C:
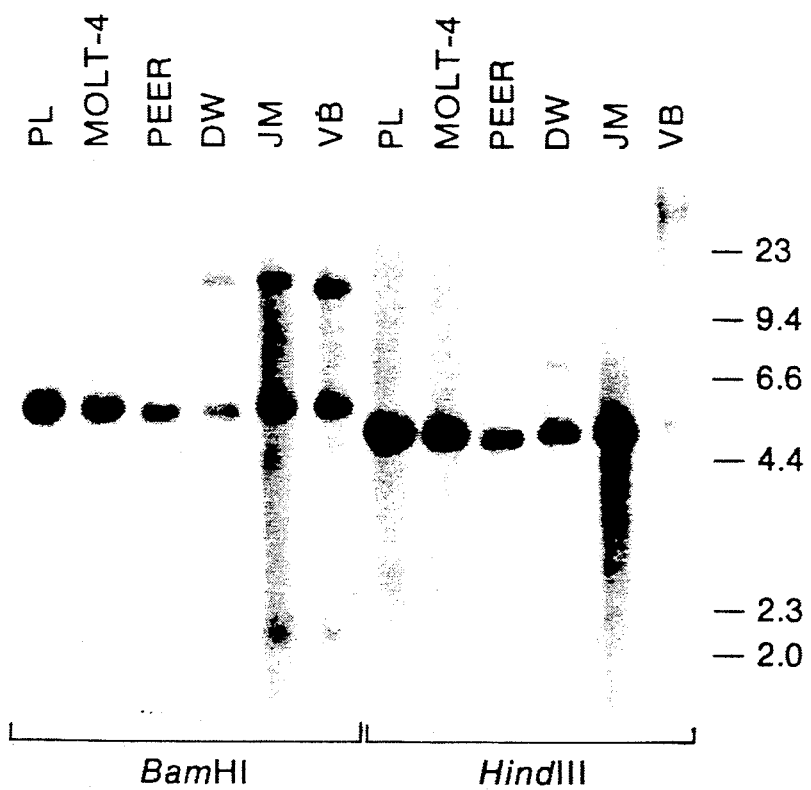

Several features are apparent. First, the pjk1.7 EcoRI-BamHI ("pjk1.7E/B") probe is derived from chromosome 10, since only hybrids that contained chromosome 10q+ (639-AD4, 648-8E10, 648-BD4) or chromosome 10 (648-BD4, 648-CC6) hybridized to the probe; hybrid 648-AC4, which contains only human chromosome 14 of the relevant chromosomes, did not hybridize. Second, the pjk1.7E/B probe segregates in the same manner as another chromosome 10 gene, TdT, when hybridized to a hybrid panel (FIG. 4B). Third, using pjk1.7E/B as a probe we have detected two different BamHI fragments (FIG. 4A). The first corresponds to a 5.7 kb BamHI fragment which represents the germline configuration and was detected in placental DNA, in PEER, and in hybrid 648-CC6. The second is a rearranged 13.9 kb BamHI fragment which was detected only in hybrids that contained human chromosome 10q+ (639-AD4, 648-8E10 and 648-BD4). The 13.9 kb BamHI rearranged fragment was detected in all three patients' DNA when the same blot was probed with pjk1.7E/B that was previously used to detect J delta rearrangements in these patients (FIGS. 1A and 4C).

Both pjk1.7E/B and pjk3.0S detected the 13.9 kb BamHI fragment by Southern blot analysis, confirming that both probes are located on the same rearranged restriction fragment. Probe pjk1.7E/B was then used to clone the relevant germline region from chromosome 10.

EXAMPLE 5

This example demonstrates that the chromosomal breakpoints of chromosome 14 are in the D-delta-2 segment, and that the breakpoints in chromosome 10 are clustered within 263 bp.

Nucleotide sequencing was conducted in M13 or from doublestranded plasmids using the dideoxy chain termination method (Sanger, F., et al., 1977, Proc. Natl. Acad. Sci. USA 74:5463-5467).

Sequence analysis at the breakpoint junctions revealed that the TCR delta sequences involved were made of the D-delta-2 segment (FIG. 5). The rearranged sequences upstream of D-delta-2 in JM's breakpoint sequence (CCCACA) probably correspond to N region diversity, indicating that the translocation occurred during an attempt to rearrange D delta to D-delta-2 segments or V to D-delta-2 segments. A heptamer-like sequence 8 bp downstream of JM's translocation point on chromosome 10 (FIG. 5) supports our hypothesis that these sequences may serve as signals for the recombinase system in joining DNA-specific sequences from two different chromosomes for the t(10;14) (q24;q11) translocation, instead of joining TCR or Ig segments on the same chromosome (Isobe, M., et al., 1985, Proc. Natl. Acad. Sci. USA 82 (17):5836-5840; Sanger, F., et al., 1977, Proc. Natl. Acad. Sci. USA 74:5463-5467).

Comparison of DW breakpoint sequences with chromosome 10 germline sequences and with JM breakpoint sequences revealed that DW's breakpoint sequence diverged exactly 4 bp 5' to JM's breakpoint. DW's breakpoint sequence is further extended 263 bp 3', where it joins the D-delta-2 segment on chromosome 14

(FIG. 5). Since we did not detect these 263 bp on the corresponding chromosome 10 germline region, we speculate that this sequence stems either from a more 3' chromosome 10 segment which was brought adjacent to the chromosome 10 (tcl-3) breakpoint region through deletion or from an insertion.

Although we have not detected a gene near the breakpoint cluster region, it is very likely that an oncogene which we call tcl-3 is further upstream, as demonstrated in some cases of Burkitt lymphoma where the translocation breakpoints occurred far downstream of the presumably involved c-myc proto-oncogene.

I claim:

1. A method for diagnosing a T-cell malignancy in a human comprising:
   isolating DNA from T-cells of the human and extracting the DNA from proteins;
   determining whether sequences of said DNA isolated from said T-cells diverge from germline sequences at a region of chromosome 10 containing a chromosome breakpoint cluster, said breakpoint cluster being located on a 5.7 kb BamHI fragment which hybridizes to pjk1.7 E/B, divergence of said sequences indicating a T-cell malignancy.

2. The method of claim 1 wherein the DNA isolated from said T-cells whose sequences diverge from the germline sequences of chromosome 10 is tested to determine whether the sequences which diverge are derived from the D-delta-2 segment of the T-cell antigen receptor delta locus on chromosome 14.

3. The method of claim 1 wherein the step of determining is performed by hybridization of the DNA isolated from said T-cells to a nucleic acid probe which is derived from a region of chromosome 10 between a chromosome breakpoint cluster associated with acute T-cell leukemia and high-grade T-cell lymphoma and a site for a restriction enzyme, wherein there are no other sites for said restriction enzyme between the breakpoint cluster and the site for the restriction enzyme, and wherein the DNA isolated from said T-cells is cleaved with said restriction enzyme to form DNA fragments, and size of a DNA fragment hybridizing to the nucleic acid probe is determined, determination of a size different from that obtained with a control DNA indicating that the germline and T-cell sequences diverge, said control DNA comprising DNA isolated from cells of the human other than the T-cells or from cells of a healthy human.

4. The method of claim 3 wherein the nucleic acid probe is derived from plasmid pJK1.7 E/B, deposited at NRRL as accession no. B-18501.

5. The method of claim 1 wherein the step of determining is performed by amplifying the DNA isolated from said T-cells in the region of the chromosome translocation junction between chromosomes 14 and 10.

6. The method of claim 5 wherein primers used to initiate the step of amplifying are derived from a 10q+ chromosome resulting from a t(10;14) (q24;q11) translocation associated with acute T-cell leukemia and high-grade T-cell lymphoma, one primer being derived from chromosome 10 sequences and one primer being derived from chromosome 14 sequences.

7. The method of claim 6 wherein one of the primers is derived from pJK1.7 E/B, deposited at NRRL as accession no. B-18501, and one of the primers is derived from the J-delta-1 region of the T-cell antigen receptor.

8. The method of claim 3 wherein the restriction enzyme is Bam HI.

9. The method of claim 2 wherein the testing to determine derivation from D-delta-2 is performed by hybridization of the DNA isolated from said T-cells to a nucleic acid probe derived from the J-delta-1 region of the T-cell antigen receptor.

10. The method of claim 9 wherein the DNA isolated from said T-cell is cleaved with a restriction enzyme which does not cleave chromosome 14 in the D-delta 2 or J-delta 1 regions nor in a region between D-delta 2 and J-delta 1 of the T-cell antigen receptor locus.

11. The method of claim 10 wherein the restriction enzyme is Bam HI.

12. The method of claim 1 wherein the malignancy is selected from the group consisting of acute T-cell leukemia and high-grade T-cell lymphoma.

13. A nucleic acid probe which hybridizes to a region of chromosome 10 between (a) a chromosome translocation breakpoint cluster associated with acute T-cell leukemia and high-grade T-cell lymphoma, and (b) a cleavage site for a restriction enzyme, wherein there are no other cleavage sites for said restriction enzyme between the breakpoint cluster and the site for the restriction enzyme.

14. The nucleic acid probe of claim 13 which is derived from pJK1.7 E/B, deposited at NRRL as accession no. B-18501.

15. A pair of single-stranded nucleic acid primers for amplification of a region of DNA containing a translocation chromosome junction associated with acute T-cell leukemia and high-grade T-cell lymphoma, one of said primers derived from chromosome 10 and one of said primers derived from chromosome 14, both of said primers hybridizing to sequences retained on a 10q+ chromosome resulting from a t(10:14) (q24;q11) translocation.

16. The method of claim 1 wherein the T-cells are isolated from a human who has received chemotherapy in order to monitor the success of the chemotherapy and wherein detection of divergence from germline sequences indicates that some malignant T-cells remain.

* * * * *